(12) United States Patent
Goble

(10) Patent No.: US 7,147,637 B2
(45) Date of Patent: Dec. 12, 2006

(54) SURGICAL INSTRUMENT

(75) Inventor: Coliin C. O. Goble, Surrey (GB)

(73) Assignee: Gyrus Group plc, Wokingham (GB)

( * ) Notice: Subject to any disclaimer, the term of this patent is extended or adjusted under 35 U.S.C. 154(b) by 114 days.

(21) Appl. No.: 10/924,840

(22) Filed: Aug. 25, 2004

(65) Prior Publication Data

US 2005/0124987 A1    Jun. 9, 2005

(30) Foreign Application Priority Data

Dec. 9, 2003   (GB) ................... 0328522.8

(51) Int. Cl.
*A61B 18/18* (2006.01)
(52) U.S. Cl. .................. 606/50; 606/51; 606/52
(58) Field of Classification Search ........ 606/205–221, 606/41, 42, 45–52
See application file for complete search history.

(56) References Cited

U.S. PATENT DOCUMENTS

| | | | |
|---|---|---|---|
| 5,693,051 A * | 12/1997 | Schulze et al. | ............... 606/51 |
| 5,709,680 A * | 1/1998 | Yates et al. | .................... 606/50 |
| 6,228,084 B1 | 5/2001 | Kirvan, Jr. | |
| 6,371,956 B1 | 4/2002 | Wilson et al. | |
| 2002/0198525 A1 | 12/2002 | Schulze et al. | |
| 2003/0163123 A1 | 8/2003 | Goble et al. | |
| 2003/0181909 A1 * | 9/2003 | Kirwan, Jr. | ................. 606/51 |

FOREIGN PATENT DOCUMENTS

DE    4303882 A1    8/1994

OTHER PUBLICATIONS

International Preliminary Report on Patentability issued in corresponding International Application No. PCT/GB2004/005056, dated Jun. 12, 2006.

* cited by examiner

*Primary Examiner*—Michael Peffley
*Assistant Examiner*—Pete Vrettakos
(74) *Attorney, Agent, or Firm*—Nixon & Vanderhye P.C.

(57) ABSTRACT

A bipolar electrosurgical instrument for cutting and sealing tissue comprises first and second jaw members movable between open and closed positions so as to be capable of grasping tissue therebetween. The first jaw member includes first and second coagulating electrodes on its inner surface, and an insulating member separating the first and second electrodes. The first jaw member also includes a third cutting electrode on an outer surface separate from the inner surface, and the second jaw member has a tissue-contacting surface which is electrically insulating over its entire surface. The electrosurgical instrument is capable of selectively causing coagulation of tissue between the first and second electrodes, and/or the cutting of tissue contacted by the third electrode.

13 Claims, 6 Drawing Sheets

SURGICAL INSTRUMENT

BACKGROUND OF THE INVENTION

This invention relates to a bipolar electrosurgical instrument, for use in the cutting and coagulating of tissue.

Two well-known classes of electrosurgical instrument are forceps-type devices, and electrosurgical cutting blades. A forceps-type device generally comprises a pair of jaws which can be opened and closed in order to grasp tissue between the jaws. An electrosurgical coagulating voltage is supplied between the jaws in order to cause the coagulation of the tissue held between the jaws. U.S. Pat. No. 5,258,006 is one example of such a device. If the cutting of tissue is desired in addition to vessel sealing, a mechanical cutting blade can be added to the forceps device, as in U.S. Pat. No. 5,445,638. More recently, an electrosurgical cutting blade can be provided as opposed to a mechanical blade, as in U.S. Pat. Nos. 6,174,309 and 6,554,829.

The other type of device is the electrosurgical cutting blade, which generally comprises two or more electrodes in close proximity to one another, as in U.S. Pat. Nos. 4,674,498, 4,850,353, 4,862,890 and 4,958,539. The present invention attempts to provide a surgical instrument combining the advantages of an electrosurgical cutting blade and a forceps-type device.

BRIEF DESCRIPTION OF THE INVENTION

Accordingly, there is provided a bipolar electrosurgical instrument for cutting and sealing tissue comprising:
  a) first and second jaw members in opposing relation relative to one another, the first jaw member having an inner surface adapted to cooperate with the inner surface of the second jaw member so as to be capable of grasping tissue therebetween, at least one of the jaw members being movable with respect to the other such that the jaw members are selectively operable between a first open position wherein the jaw members are disposed in spaced relation relative to one another, and a closed position in which the inner surface of each jaw member cooperates so as to be capable of grasping tissue therebetween;
  b) means for causing movement of the at least one jaw member so as to operate the jaw members between the open and closed positions;
  c) the first jaw member including at least first and second coagulating electrodes on its inner surface, and an insulating member separating the first and second electrodes, the first and second electrodes being capable of being connected to opposite poles of an electrosurgical generator;
  d) the first jaw member also including a third cutting electrode on an outer surface separate from the inner surface, the third electrode also being capable of being connected to one pole of an electrosurgical generator;
  e) the second jaw member having a tissue contacting surface which is electrically insulating over its entire surface;

such that the electrosurgical instrument is capable of selectively causing coagulation of tissue between the first and second electrodes, and/or the cutting of tissue contacted by the third electrode.

The present instrument can be used purely as an electrosurgical cutting blade, using the cutting electrode on the outer surface of the first jaw member. Alternatively, the instrument can be used as a coagulating forceps device, by grasping tissue between the first and second jaw members, and utilising the first and second electrodes on the first jaw member. The second jaw member is not electrosurgically active, and serves to provide the grasping pressure necessary to provide fast and effective coagulation of the tissue grasped between the jaws. The instrument is particularly suited to surgical procedures on the tonsils and adenoids, in particular the tonsils in which surgery often requires the sealing of the tonsular artery.

Preferably the insulating member and the first and second coagulating electrodes are flush with one another along that the inner surface of the first jaw member. Typically the inner surface of the first jaw member presents a planar surface, although ridges may conveniently be provided on one or both jaws in order to improve the purchase exerted on the tissue. This allows the effective coagulation of tissue grasped between the jaws. Conveniently, the first jaw member comprises an electrically insulating central portion constituting the insulating member, with electrically conductive portions attached thereto on either side in order to constitute the first and second electrodes.

In one convenient arrangement, the electrically insulating central portion extends through the first jaw member from the inner surface to the outer surface thereof. The electrically insulating central portion conveniently has a longitudinal recess therein, in communication with the outer surface, and the third cutting electrode is located in the longitudinal recess. In this way, the cutting electrode is provided on the reverse face of the instrument to that used in order to perform the coagulation of tissue. The cutting face of the device can therefore be designed so as to be optimum for cutting, without having to provide a compromise design on a portion of the device also used to perform tissue coagulation.

The second jaw member is not electrosurgically active, and is designed so as to provide the necessary pressure on the tissue during coagulation. Conveniently, the second jaw member is integrally formed of an electrically insulating material, but may also be formed of an electrically conductive material with an electrically insulating portion attached thereto in order to form the tissue-contacting surface. Tissue coagulation occurs between the first and second coagulating electrodes positioned on the first jaw member, across the insulating member located therebetween. The electrically insulating second jaw member hold the tissue against the first and second electrodes, and applies pressure to the tissue in order to allow for fast and effective tissue coagulation.

According to one convenient arrangement, the second jaw is longitudinally movable between a first position in which the tissue contacting surface is adjacent the inner surface of the first jaw member, and a second position in which the second jaw member is retracted proximally from the first jaw member. In this way, the second jaw member can be retracted out of the way of the first jaw member, for times when the user of the instrument merely intends the device to be used as a cutting instrument. Additionally or alternatively, the second jaw member is detachably connected to the first jaw member.

In one convenient arrangement the first and second jaw members form part of first and second arms respectively. Where the second jaw member is detachable from the first jaw member, the second arm is capable of being clipped on to, and removed from, the first arm. As with the retractable jaw member, this arrangement allows the first jaw member to be used on its own as a cutting device, without the second jaw member, for procedures in which only tissue cutting is required.

In a further arrangement, the second arm is provided with a lumen extending from the distal end of the arm to the proximal end thereof, the lumen being capable of being connected to a source of suction. In this way, excess matter such as smoke, blood or tissue debris can be aspirated from the surgical site, though the lumen provided in the second arm. This may be particularly useful in procedures such as those performed on the tonsils or adenoids, in which the procedure is being performed in a very small space and it may be difficult to allow for the introduction of additional instruments such as suction or fluid delivery devices.

BRIEF DESCRIPTION OF THE DRAWINGS

The invention will now be described in further detail, by way of example only, with reference to the accompanying drawings, in which.

DETAILED DESCRIPTION OF THE INVENTION

Figure 1:
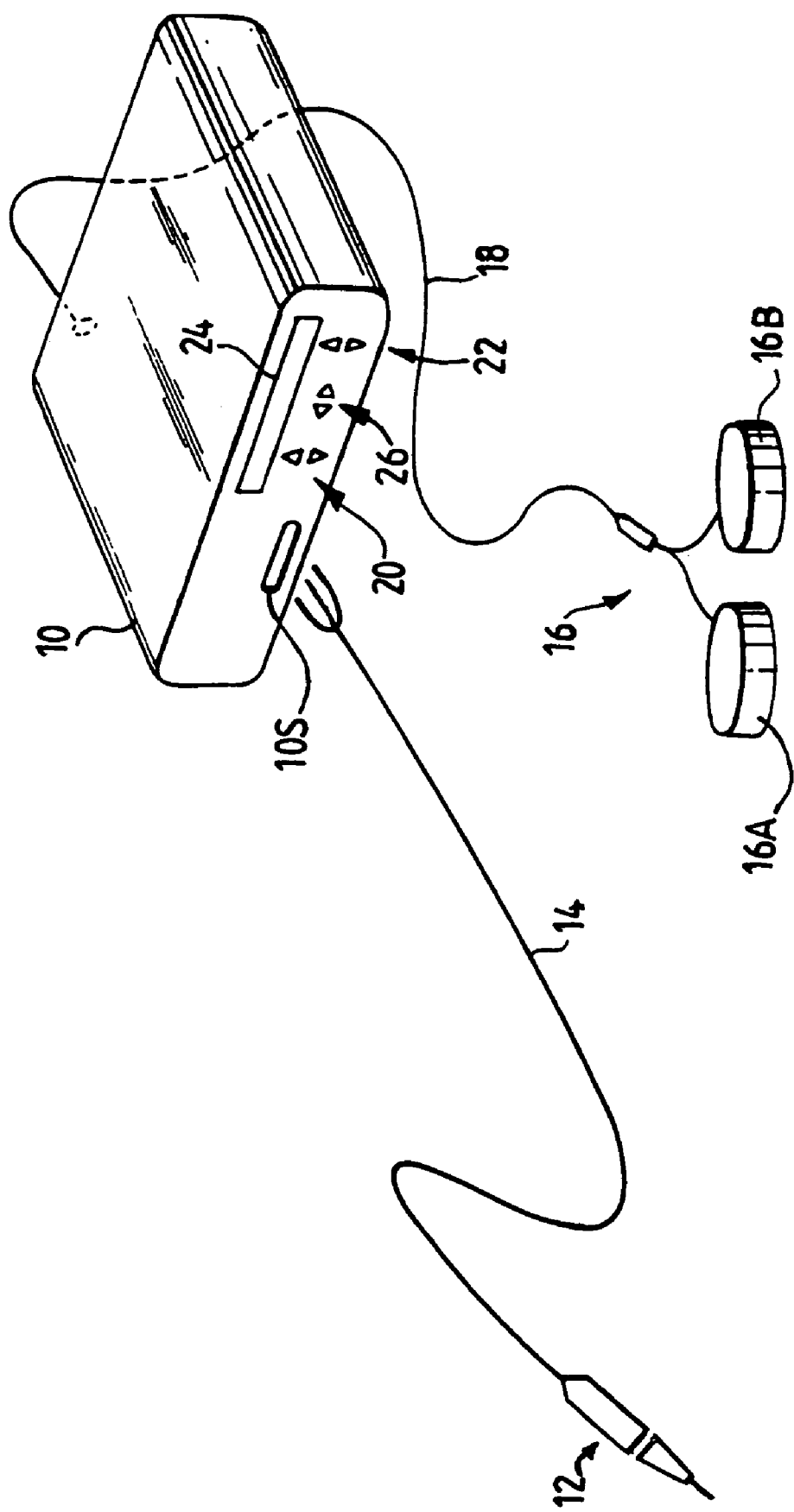
FIG. 1 is a schematic diagram of an electrosurgical system for an electrosurgical instrument in accordance with the present invention.

Referring to FIG. 1, a generator 10 has an output socket 10S providing a radio frequency (RF) output for an instrument 12 via a connection cord 14. Activation of the generator 10 may be performed from the instrument 12 via the connection cord 14 or by means of a footswitch unit 16, connected to the rear of the generator by a footswitch connection cord 18. In the illustrated embodiment, the footswitch unit 16 has two footswitches 16A and 16B for selecting a coagulation mode and a cutting mode of the generator 10 respectively. The generator front panel has push buttons 20 and 22 for respectively setting coagulation and cutting power levels, which are indicated in a display 24. Push buttons 26 are provided as an alternative means for selection between coagulation and cutting modes.

Figure 2:
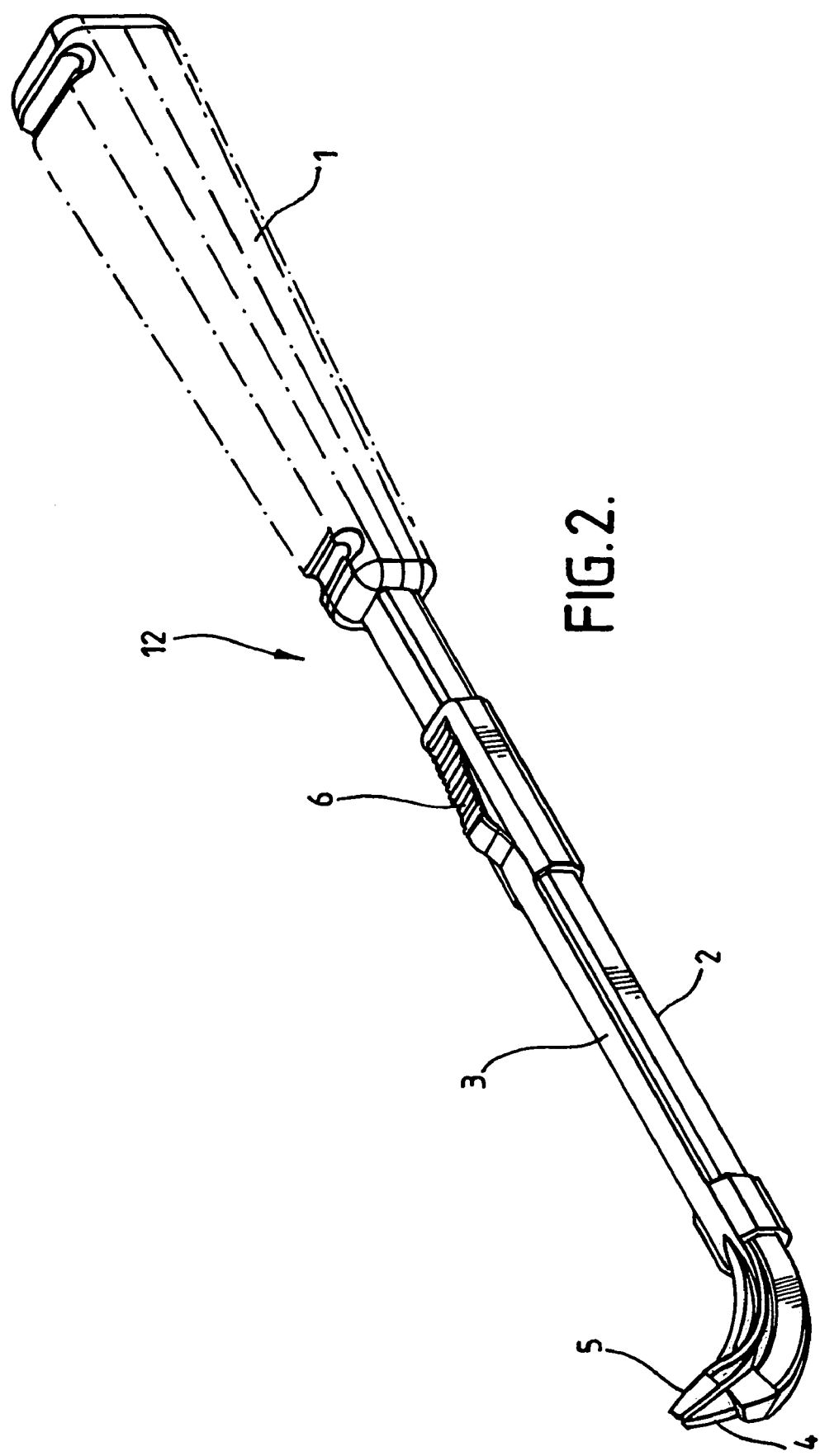
FIG. 2 is a perspective view of an electrosurgical instrument in accordance with the present invention.

FIG. 2 shows one arrangement of instrument 12. The instrument comprises a handle 1 from which depends a first arm 2 and a second arm 3 attached thereto. The first arm 2 terminates in a first jaw member 4, while the second arm 3 terminates in a second jaw member 5. The second arm 3 is removably clipped over the first arm 2, and is longitudinally slideable thereon. Longitudinal movement of the second arm 3, by means of finger button 6, varies the distance between the first and second jaw members 4 and 5.

Figure 3:
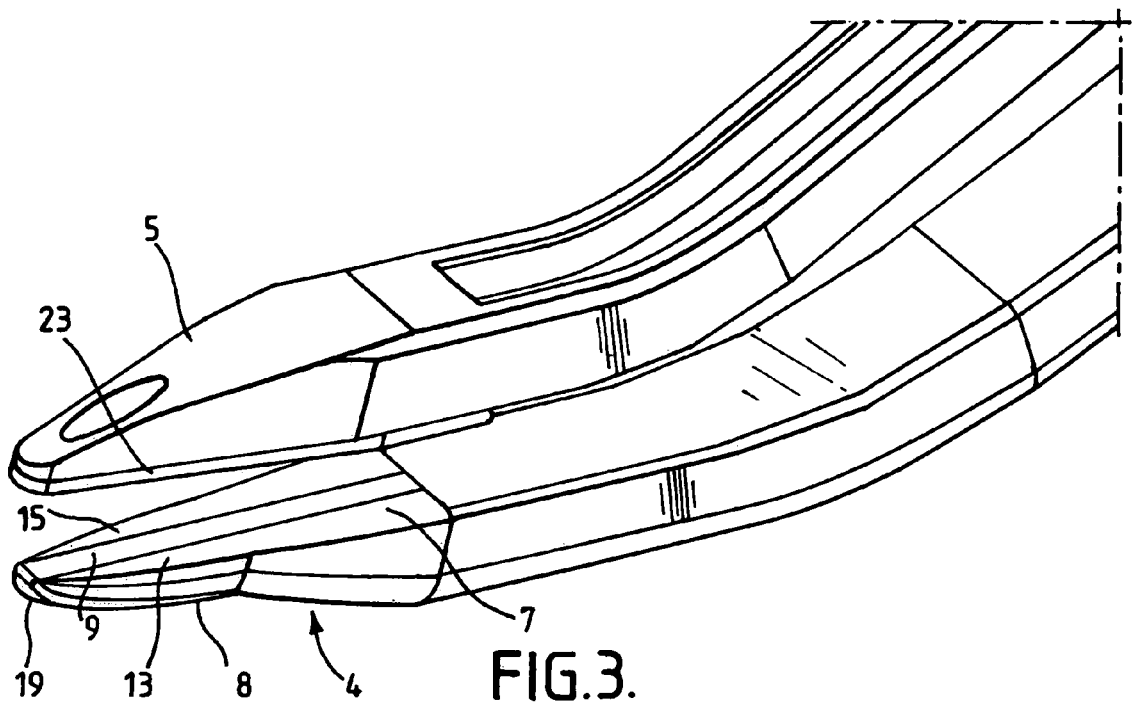
FIG. 3 is an enlarged view of a part of the instrument of FIG. 2.
Figure 4:
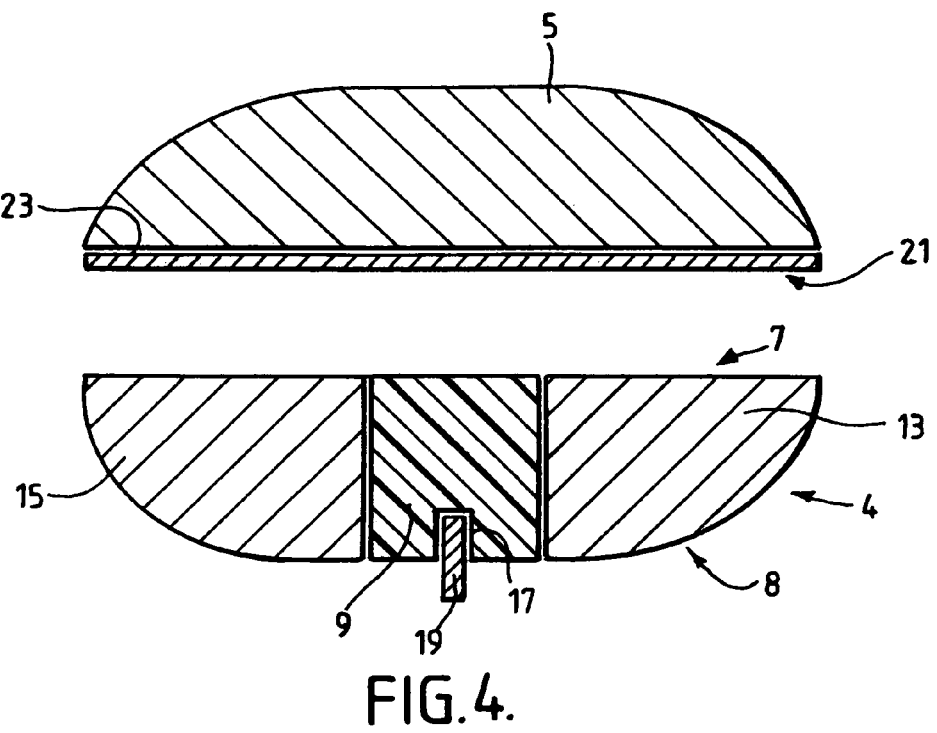
FIG. 4 is a schematic cross-sectional view of that part of the instrument shown in FIG. 3.

Referring to FIGS. 3 & 4, the first jaw member 4 has a substantially planar inner surface 7, and a curved outer surface 8. The jaw member 4 comprises a central block 9 of insulating material, flanked on either side by first and second electrode structures 13 and 15, formed of an electrically-conductive material such as copper. The electrode structures 13 and 15 are bonded to the block 9 by means of an adhesive such as Epotek™, or may alternatively be secured by means of pins, staples or other mechanical means. The block 9 extends through the jaw member 4 from the inner surface 7 to the outer surface 8, and has a longitudinal recess 17 in communication with the outer surface 8. Located within the recess 17, again secured by a suitable adhesive, is a cutting electrode 19. The cutting electrode 19 is formed of an electrically-conductive metallic material such as stainless steel or tantalum, and extends from the recess 17 to project marginally beyond the curved outer surface 8.

The second jaw member 5 is formed of a rigid substrate material such as steel, plastics, or steel-reinforced plastics material. The second jaw member 5 also has an inner surface 21, and this inner surface is covered by a plate 23 formed of an electrically-insulating material such as ceramic, silicone rubber, or a silicone rubber-coated ceramic.

The operation of the instrument of FIGS. 2 to 4 will now be described. In a cutting mode, the instrument 12 is manoeuvred such that the cutting electrode 19 is in contact with tissue. A cutting electrosurgical voltage is supplied from the generator 10, one pole of the generator being connected to the cutting electrode 19, and the other pole to electrodes 13 and 15. Arcing occurs between the cutting electrode 19 and the tissue, and current flows through the tissue to whichever of the electrodes 13 and 15 that is also in contact with the tissue. The cutting of the tissue in this way is more particularly described in our co-pending patent application WO03/055402.

When the instrument 12 is to be used to coagulate tissue, for example following the cutting of tissue as described above, the instrument is manoeuvred such that the tissue to be coagulated is located between the first and second jaw members 4 and 5. The finger button 6 is operated so as to close the second jaw member 5 against the first jaw member 4, thereby trapping the tissue to be coagulated between the jaw members. As pressure is applied to the tissue by the jaw members 4 and 5, a coagulating voltage is supplied from the generator 10, one pole of the generator being connected to the electrode 13 and the other to electrode 15. Current flows between the electrodes 13 and 15 through the tissue and across the insulating block 9, causing the tissue trapped between the jaw members to be coagulated.

The instrument 12 can also be used in a blended cutting and coagulation mode, in which case an electrosurgical cutting voltage is combined with an electrosurgical coagulating voltage, the cutting voltage being supplied to the cutting electrode 19, and the coagulating voltage between the electrodes 13 and 15. This blended mode of operation is described in our co-pending patent application U.S. 2003-0139741, and will not be described further herein.

Figure 5:
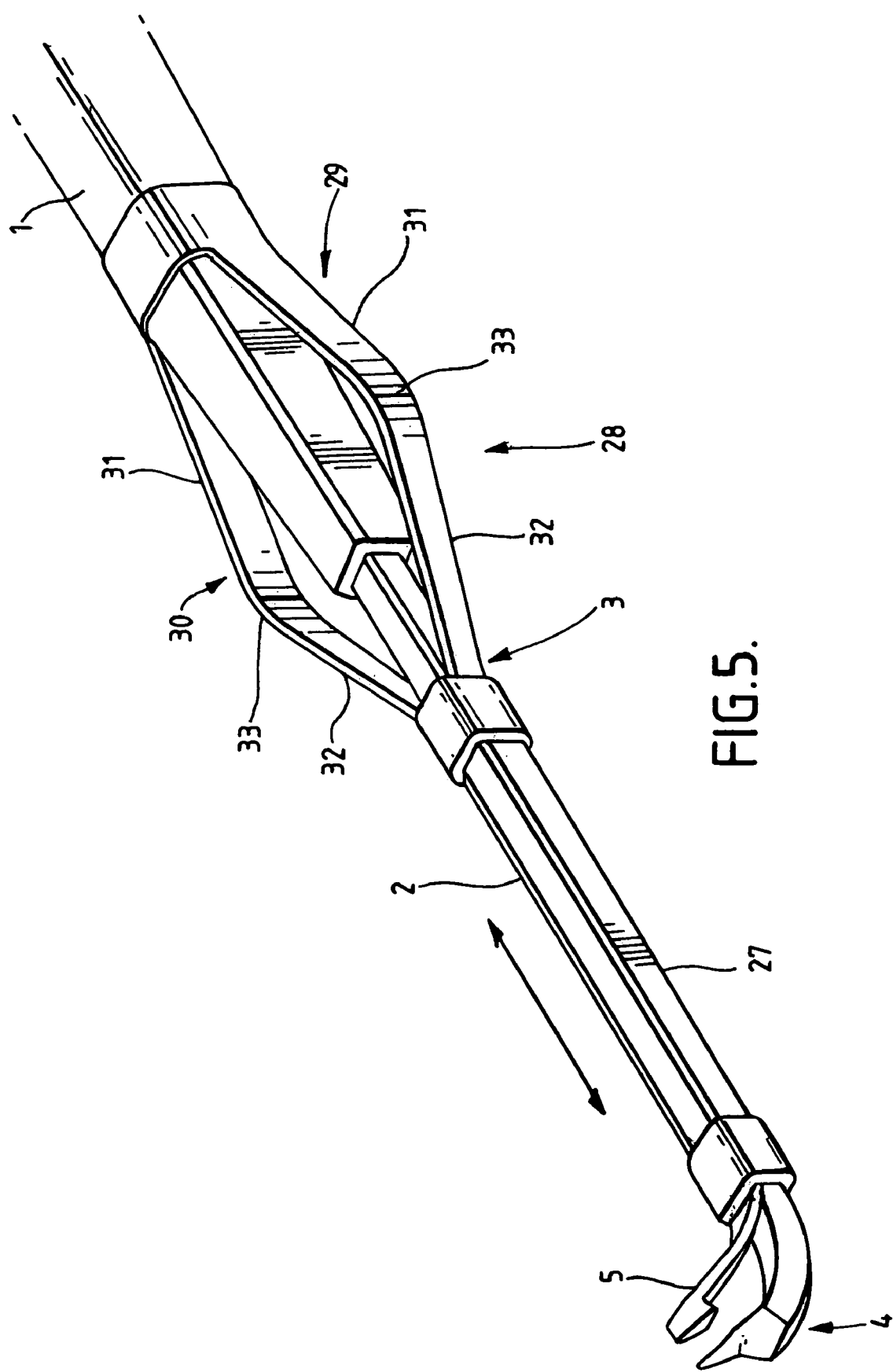
FIG. 5 is a perspective view of an alternative embodiment of instrument in accordance with the invention.

Referring to FIG. 5, an alternative embodiment of instrument 12 is shown, with like elements being designated with like reference numerals. The handle 1 and the first arm 2 are substantially as before, and the second arm 3 is again longitudinally slidable with respect to the first arm 2. The second arm 3 comprises a longitudinal portion 27 and a flexible portion 28, the flexible portion consisting of left and right arm members 29 and 30. Each arm member 29, 30 comprises a proximal arm element 31 and a distal arm element 32, connected by an elbow portion 33. The arm members 29, 30 are biased into a position in which the arm elements 31 and 32 are angled with respect to one another.

When the user of the instrument needs to close the jaw member 5 against the jaw member 4, the user squeezes together the arm members 29 and 30, straightening the elbow portions 33 such that the arm elements 31 and 32 are linearly aligned one with the other. This causes the longitudinal portion 27 of the second arm 3 to slide distally down the first arm 2, moving the second jaw member 5 against the first jaw member 4. This arrangement has the advantage that the pincer-like movement of the user's fingers causes a corresponding movement of the jaw member 5. Thus the opening and closing operation of the instrument 12 is intuitive for the user of the instrument, with the jaws moving in response to a corresponding movement of the user's fingers.

Figure 6:
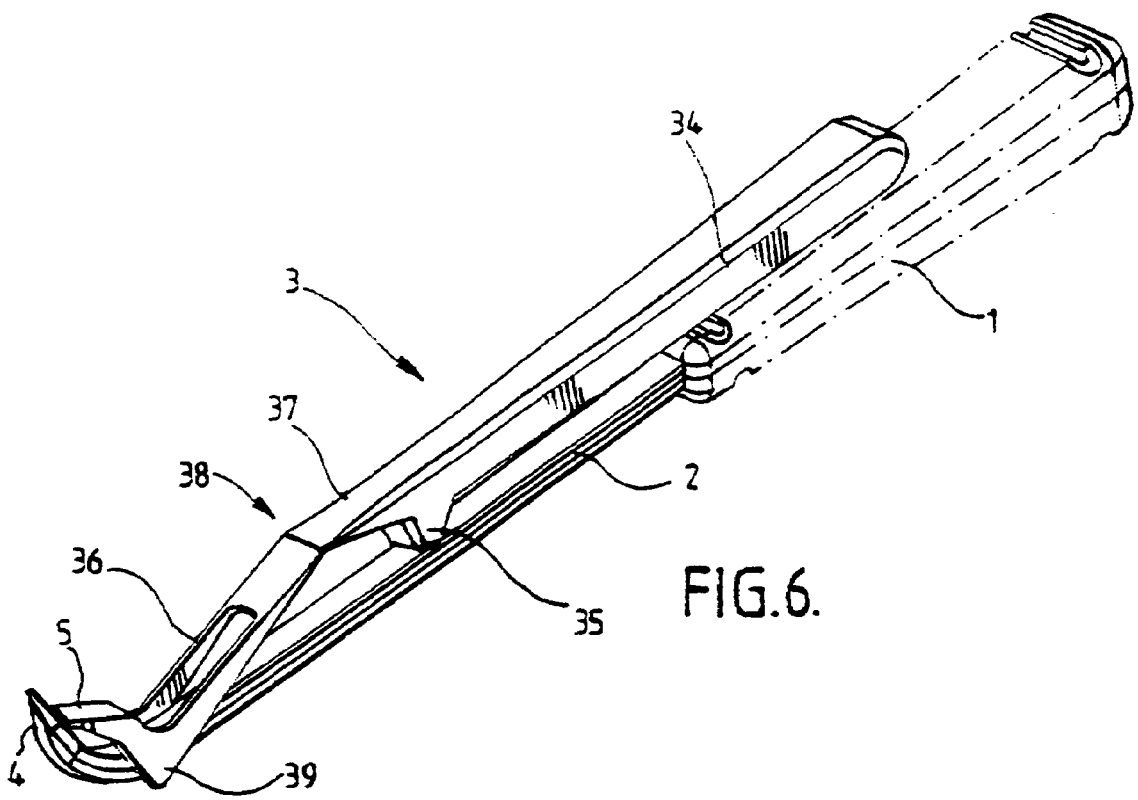
FIG. 6 is a perspective view of a further alternative embodiment of instrument in accordance with the invention.

FIGS. 6 and 7 show a further embodiment of instrument 12, this time using a pivotable second arm 3. The second arm 3 comprises a stem portion 34 with a fulcrum point 35 arranged to bear against the first arm 2. Beyond the fulcrum point 35, the second arm 3 comprises a distal section 36 and a proximal section 37, joined by a hinge 38. The second arm 3 is typically formed of a plastics material, and the hinge 38 is integrally formed in the plastics material in the form of a "living hinge". The distal section 36 is itself movable about a pivot point 39 attached to the first arm 2.

Figure 7A:
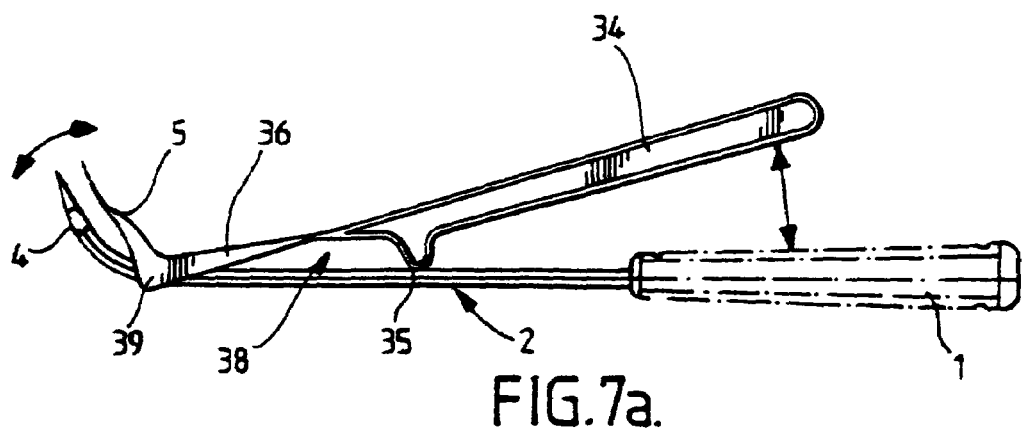
FIGS. 7a and 7b are side views of the instrument of FIG. 6, shown in its open and closed position respectively.
Figure 7B:
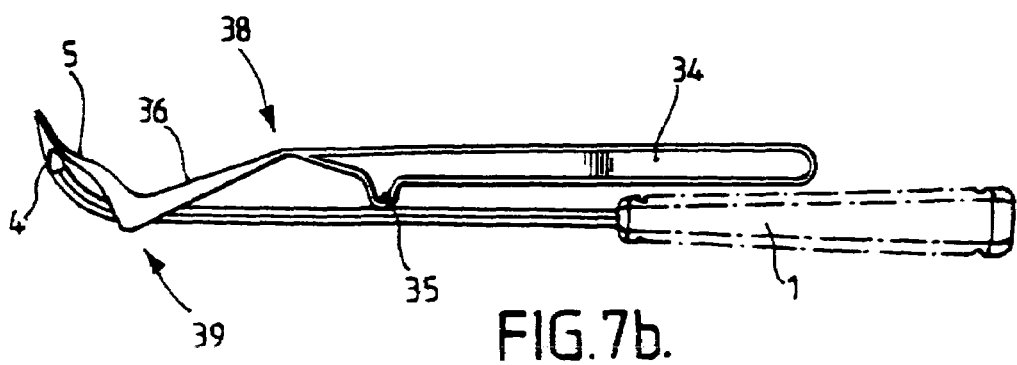

The operation of the instrument is shown in FIGS. 7a and 7b. To move the jaw members 4 and 5 to their open position, the stem portion 34 is moved away from the handle 1, as shown in FIG. 7a. This causes the distal section 36 to pivot about the pivot point 39 in order to move the jaw member 5 away from the jaw member 4. Conversely, to move the jaw members 4 and 5 to their closed position, the stem portion 34 is moved towards the handle 1 as shown in FIG. 7b. This causes the distal section 36 to pivot about the pivot point 39 in order to move the jaw member 5 towards the jaw member 4. The second arm 3 is easily detachable from the first arm 4, so that the instrument 12 can be used solely as a cutting instrument without the encumbrance of the second arm.

Figure 8:
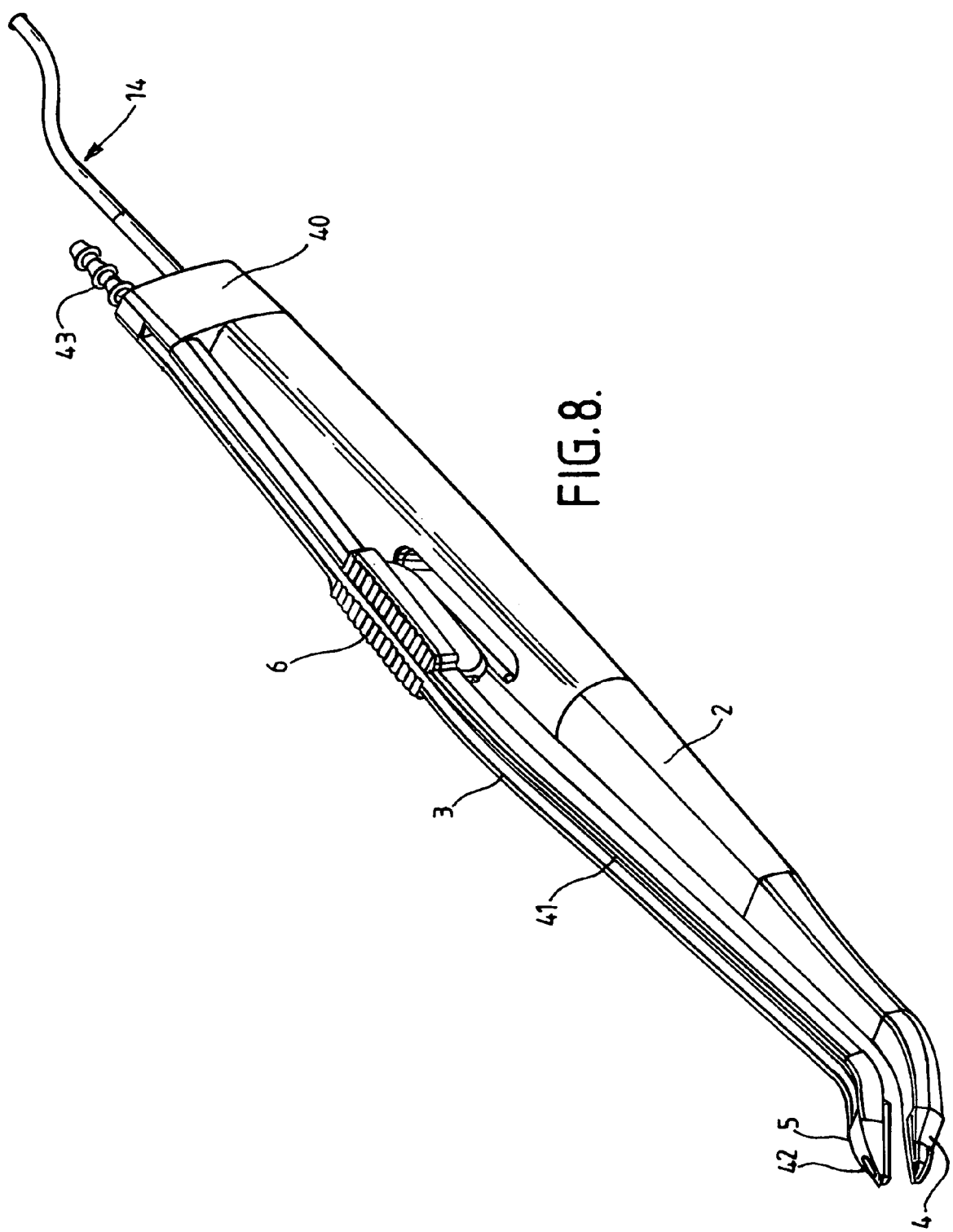
FIG. 8 is a perspective view of a further alternative embodiment of instrument in accordance with the invention.

FIG. 8 shows a further alternative embodiment of instrument 12, which is capable of delivering suction to the surgical site. In the instrument of FIG. 8, the second arm 3 is a cantilever arm, cantilevered from a collar 40 attaching the second arm 3 to the first arm 2. The second arm 3 is biased such that it is generally positioned with the second jaw member 5 spaced from the first jaw member 4. The second arm 3 is moved towards the first arm 2, to close the jaw member 5 against the jaw member 4, by pressure on a finger button 6 on the second arm.

The second arm 3 is also provided with a lumen 41 running the entire length of the arm, and exiting at its distal end in an aperture 42 on the outer surface of the second jaw member 5. The lumen 41 terminates at its proximal end in a suction connector 43, which is, in use, connected to a conventional source of suction. In use, the device can be used to cut or coagulate tissue as previously described, while smoke, fluid or tissue debris is evacuated from the surgical site via the lumen 41.

While the invention has been described in connection with several embodiments, it is to be understood that the invention is not to be limited to the disclosed embodiments, but on the contrary, is intended to cover various modifications and equivalent arrangements included within the spirit and scope of the appended claims.

What is claimed is:

1. A bipolar electrosurgical instrument for cutting and sealing tissue, the instrument comprising:
   a) first and second jaw members in opposing relation relative to one another, the first jaw member having an inner surface adapted to cooperate with the inner surface of the second jaw member so as to be capable of grasping tissue therebetween, at least one of the jaw members being movable with respect to the other such that the jaw members are selectively operable between an open position wherein the jaw members are disposed in spaced relation relative to one another, and a closed position in which the inner surface of each jaw member cooperates so as to be capable of grasping tissue therebetween;
   b) means for causing movement of the at least one jaw member so as to operate the jaw members between the open and closed positions;
   c) the first jaw member including at least first and second coagulating electrodes on its inner surface, and an insulating member separating the first and second electrodes, the first and second electrodes being capable of being connected to opposite poles of an electrosurgical generator;
   d) the first jaw member also including a third, cutting electrode on an outer surface separate from the inner surface, the third electrode also being capable of being connected to one pole of an electrosurgical generator; and
   e) the second jaw member having a tissue-contacting surface which is electrically insulating over its entire surface;
   such that the electrosurgical instrument is capable of selectively causing coagulation of tissue between the first and second electrodes, and/or the cutting of tissue contacted by the third electrode.

2. An electrosurgical instrument according to claim 1, wherein the insulating member and the first and second coagulating electrodes are flush with one another along the inner surface of the first jaw member.

3. An electrosurgical instrument according to claim 2, wherein the inner surface of the first jaw member presents a planar surface.

4. An electrosurgical instrument according to claim 1, wherein the first jaw member comprises an electrically-insulating central portion constituting the insulating member, with electrically-conductive portions attached thereto on either side in order to constitute the first and second electrodes.

5. An electrosurgical instrument according to claim 1, wherein the second jaw member is integrally formed of an electrically-insulating material.

6. An electrosurgical instrument according to claim 5, wherein the second jaw member is formed of an electrically-conductive material, and has an electrically-insulating portion attached thereto in order to form the tissue-contacting surface.

7. An electrosurgical instrument according to claim 1, wherein the second jaw member is detachably connected to the first jaw member.

8. An electrosurgical instrument according to claim 7, wherein the second arm is capable of being clipped on to, and removed from, the first arm.

9. An electrosurgical instrument according to claim 1, wherein the first and second jaw members form part of first and second arms respectively.

10. An electro surgical instrument according to claim 9, wherein the second arm is provided with a lumen extending from the distal end of the arm to the proximal end thereof, the lumen being capable of being connected to a source of suction.

11. A bipolar electrosurgical instrument for cutting and sealing tissue, the instrument comprising:
   a) first and second jaw members in opposing relation relative to one another, the first jaw member having an inner surface adapted to cooperate with the inner surface of the second jaw member so as to be capable of grasping tissue therebetween, at least one of the jaw members being movable with respect to the other such that the jaw members are selectively operable between an open position wherein the jaw members are disposed in spaced relation relative to one another, and a closed position in which the inner surface of each jaw member cooperates so as to be capable of grasping tissue therebetween;
   b) means for causing movement of the at least one jaw member so as to operate the jaw members between the open and closed positions;
   c) the first jaw member including at least first and second coagulating electrodes on its inner surface, and an insulating member separating the first and second electrodes, the first and second electrodes being capable of being connected to opposite poles of an electrosurgical generator;
   d) the first jaw member also including a third, cutting electrode on an outer surface separate from the inner surface, the third electrode also being capable of being connected to one pole of an electrosurgical generator; and
   the second jaw member having a tissue-contacting surface which is electrically insulating over its entire surface;
   the electrosurgical instrument being capable of selectively causing coagulation of tissue between the first and second electrodes, and/or the cutting of tissue contacted by the third electrode;
   wherein the first jaw member comprises an electrically-insulating central portion constituting the insulating member, with electrically-conductive portions attached thereto on either side in order to constitute the first and second electrodes; and
   wherein the electrically-insulating central portion extends through the first jaw member from the inner surface to the outer surface thereof.

12. An electrosurgical instrument according to claim 11, wherein the electrically-insulating central portion has a longitudinal recess therein, in communication with the outer surface, and the third cutting electrode is located in the longitudinal recess.

13. A bipolar electrosurgical instrument for cutting and sealing tissue, the instrument comprising:
   a) first and second jaw members in opposing relation relative to one another, the first jaw member having an inner surface adapted to cooperate with the inner surface of the second jaw member so as to be capable of grasping tissue therebetween, at least one of the jaw members being movable with respect to the other such that the jaw members are selectively operable between an open position wherein the jaw members are disposed in spaced relation relative to one another, and a closed position in which the inner surface of each jaw member cooperates so as to be capable of grasping tissue therebetween;
   b) means for causing movement of the at least one jaw member so as to operate the jaw members between the open and closed positions;
   c) the first jaw member including at least first and second coagulating electrodes on its inner surface, and an insulating member separating the first and second electrodes, the first and second electrodes being capable of being connected to opposite poles of an electrosurgical generator;
   the first jaw member also including a third, cutting electrode on an outer surface separate from the inner surface, the third electrode also being capable of being connected to one pole of an electrosurgical generator; and
   the second jaw member having a tissue-contacting surface which is electrically insulating over its entire surface;
   the electrosurgical instrument being capable of selectively causing coagulation of tissue between the first and second electrodes, and/or the cutting of tissue contacted by the third electrode;
   wherein the second jaw is longitudinally movable between a first position in which the tissue contacting surface is adjacent to the inner surface of the first jaw member, and a second position in which the second jaw member is retracted proximally from the first jaw member.

* * * * *